United States Patent [19]
Fukaya

[11] Patent Number: 5,420,716
[45] Date of Patent: May 30, 1995

[54] SURGICAL MICROSCOPE APPARATUS

[75] Inventor: Takashi Fukaya, Hachiouji, Japan

[73] Assignee: Olympus Optical Co., Ltd., Tokyo, Japan

[21] Appl. No.: 83,274

[22] Filed: Jun. 29, 1993

[30] Foreign Application Priority Data

Jul. 1, 1992 [JP] Japan .................. 4-174431

[51] Int. Cl.6 ............................. G02B 21/24
[52] U.S. Cl. .................. 359/368; 359/372; 359/383; 359/388; 359/393
[58] Field of Search ............... 359/368, 379, 382, 383, 359/389, 390, 384, 391, 392, 393; 351/210

[56] References Cited

U.S. PATENT DOCUMENTS

| | | | |
|---|---|---|---|
| 4,395,731 | 7/1983 | Schoolman | 359/379 |
| 4,991,947 | 2/1991 | Sander et al. | 359/375 |
| 5,048,941 | 9/1991 | Hamada et al. | 359/368 |
| 5,094,522 | 10/1992 | Sourdille et al. | 351/210 |

FOREIGN PATENT DOCUMENTS

| | | |
|---|---|---|
| 53-23168 | 7/1978 | Japan . |
| 61-172552 | 8/1986 | Japan . |
| 3-5810 | 1/1991 | Japan . |
| 482439 | 1/1970 | Switzerland . |

*Primary Examiner*—Joseph A. Popek
*Assistant Examiner*—Huan Hoang
*Attorney, Agent, or Firm*—Cushman, Darby & Cushman

[57] ABSTRACT

A surgical microscope apparatus comprising a supporting device for suspending a microscope, a detecting device for detecting a location of a pupil of an observer relative to an observing pupil of the microscope and a drive controller for automatically moving the microscope, on the basis of a result detected by the detecting device, so that the observing pupil of the microscope is coincident with the pupil of the observer. This surgical microscope apparatus requires no manual handling for shifting the microscope and permits a continuous observation of a visual field without fail.

7 Claims, 9 Drawing Sheets

SURGICAL MICROSCOPE APPARATUS

BACKGROUND OF THE INVENTION a) Field of the Invention

The present invention relates to a surgical microscope apparatus which comprises a microscope and a supporting device for supporting the microscope in a shiftable manner.

b) Description of the Prior Art

A microscope apparatus to be used for microsurgery generally consists of a microscope which permits observation of a part to be operated on, and a supporting device which permits shifting the microscope to desired locations and sustaining the microscope at the locations. A variety of apparatus' have hitherto been made for the supporting device so that it can provide the desired visual fields for an operator through simple handling procedures during surgical operations.

Japanese Patent Preliminary Publication No. Sho 53-23168, for example, discloses a supporting device as shown in FIG. 1 wherein a turning moment of a microscope M is balanced with that of balancing weights Ga and Gb, and a shifting mechanism for the microscope M is fixed by using an electromagnetic lock attached to bearings BL1 through BL6. This supporting device permits an operator to shift the microscope M to a desired angle and a desired location by exerting a very weak force, and hold the microscope M in this state.

Furthermore, Swiss Patent No. 482 439 discloses a supporting device which is configured so as to permit electrically shifting a microscope by using control members disposed on a head rest. This supporting device makes it possible for an operator to shift the microscope without using his hands.

Furthermore, Japanese Patent Preliminary Publication No. Sho 61-172552 proposes a supporting device which detects a direction of a line of vision of an observer within an observing visual field and controls a microscope shifting means on the basis of a result obtained by the detection so that a center of an object to be observed which is located in the direction of the line of vision is coincident with a center of the observation visual field of a microscope. This supporting device makes it possible for an operator to shift the microscope to a desired location simply by changing a direction of vision of the operator.

The supporting device disclosed by Japanese Patent Preliminary Publication No. Sho 53-23168 obliges an operator to use his hand for shifting the microscope M and forces him to interrupt a surgical operation when he requires to shift the microscope during the surgical operation. In such a case, it is necessary to take measures for interrupting the surgical operation and such interruption at a serious step of a surgical operation may be fatal to the life of a patient.

A supporting device of the type disclosed by Swiss Patent No. 482 439 is configured so as to operate the control members by using a head of an operator and permit shifting a microscope without interrupting a surgical operation. When the microscope is set at a high magnification level, however, the microscope has a small diameter of an observing pupil and a slight deviation of an eye of an operator from an eyepiece lens may cause a loss of sight of an observation visual field, thereby constituting a danger for a patient.

Moreover, the supporting device disclosed by Japanese Patent Preliminary Publication No. Sho 61-172552 is effective to shift a microscope for observing a part to be operated on which is located within an observation visual field, but obliges an operator to direct his line of vision continuously outside the visual field when the microscope is to be shifted to a part to be operated which is located outside the visual field, thereby requiring a rather long time for shifting the microscope, having a tendency to tire an operator and therefore not being suited for practical use.

SUMMARY OF THE INVENTION

A primary object of the present invention is to provide a surgical microscope apparatus which requires no use of the hands for shifting a microscope and is capable of maintaining a visual field without fail even when shifting the microscope.

The surgical microscope apparatus according to the present invention comprises a microscope, a supporting device which supports a microscope shifting device for shifting the microscope, a means for coinciding an observing pupil of the microscope with a pupil of an observer, a detecting means for detecting a location of the pupil of the observer relative to the microscope and a control means for operating the supporting device on the basis of a result detected by the detecting means.

The surgical microscope apparatus according to the present invention is configured to preliminarily coincide the observing pupil of the microscope with the pupil of the observer, store a location of the pupil of the observer, detect a deviation of a current location of the pupil of the observer from the stored location, and shift the microscope and the supporting device by driving and controlling, on the basis of the result detected by the detecting means, the microscope shifting device so that the observing pupil of the microscope is coincident with the current location of the pupil of the observer. Since the microscope and the supporting device are shifted electrically on the basis of a detection signal obtained by detecting the deviation of the location of the pupil of the observer from the observing pupil of the microscope, the surgical microscope apparatus according to the present invention makes it possible to shift the microscope securely and speedily to a desired location without requiring the observer to use his hand.

The present invention makes it possible to provide a surgical microscope apparatus which eliminates the fear of losing sight of a visual field when shifting the microscope, and can be operated easily.

DESCRIPTION OF THE PREFERRED EMBODIMENTS

Now, the first embodiment of the surgical microscope apparatus according to the present invention will be described below with reference to FIG. 2 through FIG. 5.

Figure 1:
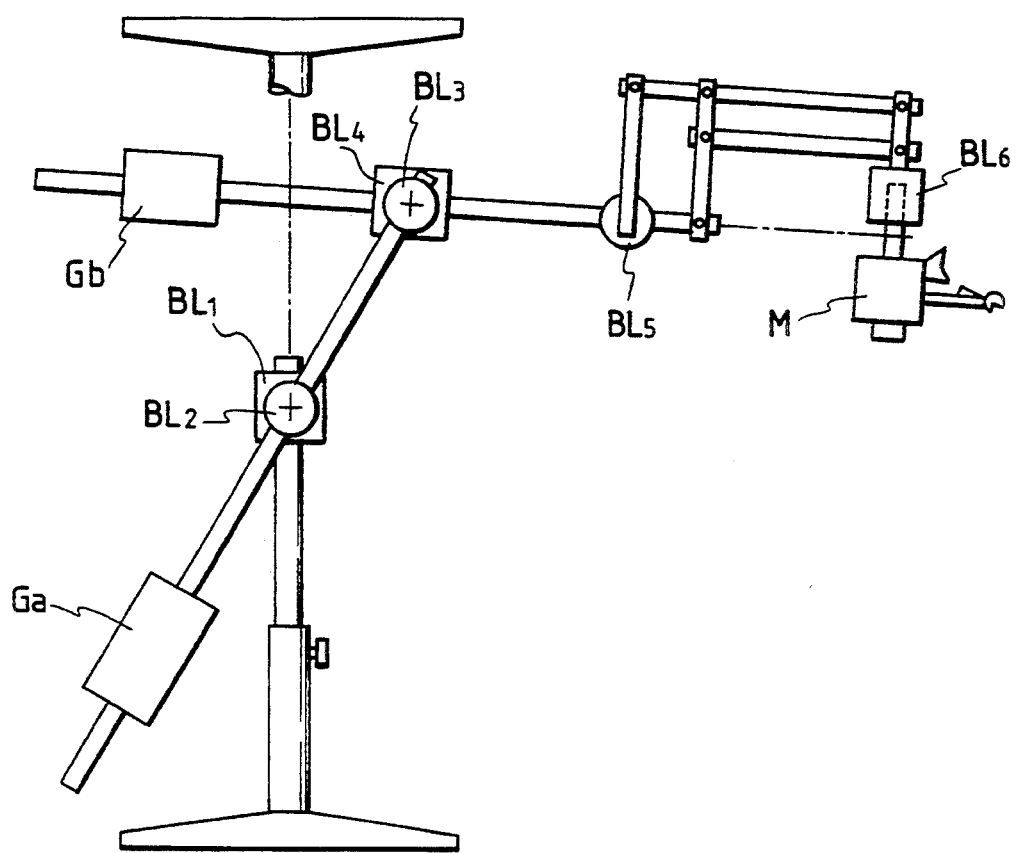
FIG. 1 is an external view illustrating a conventional surgical microscope.
Figure 2:
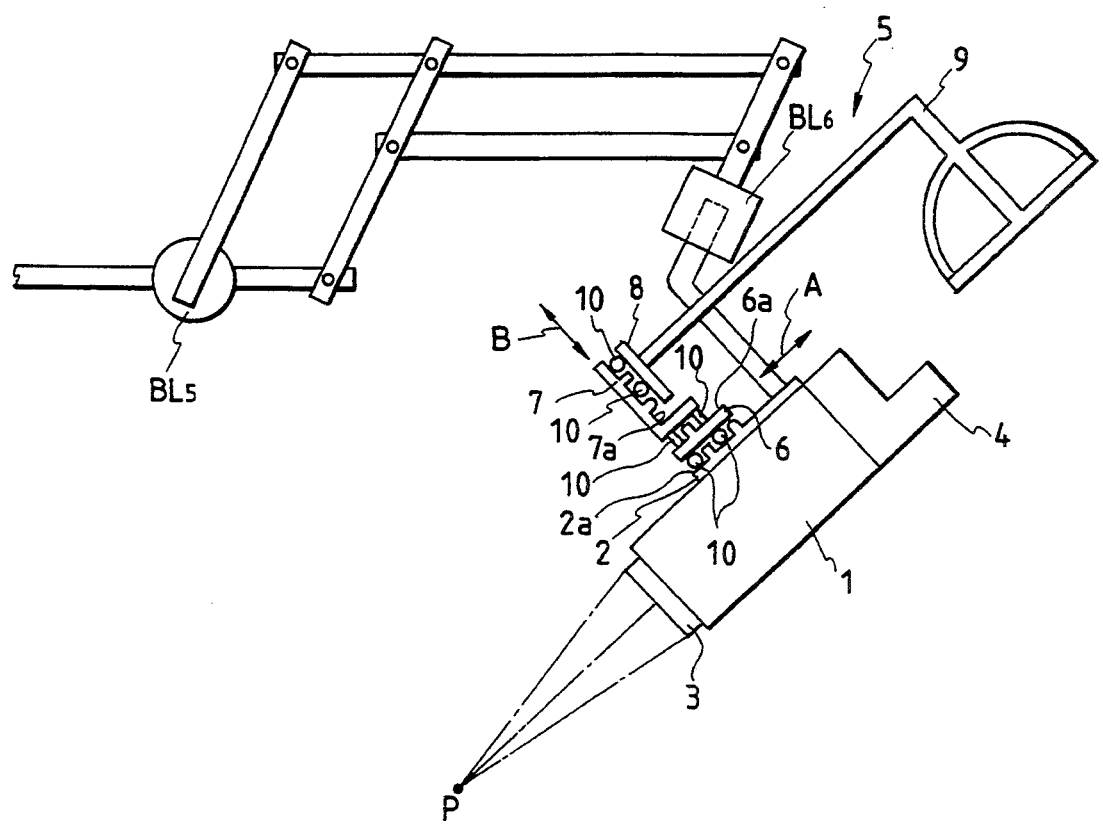
FIG. 2 is an external view illustrating a portion of a supporting device, a microscope shifting device and a microscope which are to be used in a first embodiment of the surgical microscope apparatus according to the present invention.

In FIG. 2, the reference numeral 1 represents a microscope which is attached to a supporting device such as that shown in FIG. 1 by way of an attaching member 2, the reference numerals 3 and 4 designate an objective lens and an eyepiece lens respectively which are attached to the microscope 1, and the reference numeral 5 denotes a pupil location detecting device which consists of a first shifting member 6, a second shifting member 7, a third shifting member 8 and a head rest 9 fixed to the third shifting member 8, and functions to detect a location of a pupil of an observer. The first shifting member 6 is disposed by way of a roller guide 10 so as to be freely shiftable relative to a surface 2a of the attaching member 2 in a direction indicated by an arrow A, the second shifting member 7 is disposed by way of a roller guide 10 so as to be freely shiftable relative to a surface 6a of the first shifting member 6 in a direction perpendicular to the surface of the drawing and the third shifting member 8 is disposed by way of a roller guide 10 so as to be freely shiftable relative to a surface 7a of the second shifting member 7 in a direction indicated by an arrow B, whereas locations of these shifting members can be sustained relative to the shifting planes thereof by piston shafts 14a, 14b and 14c respectively.

Figure 3:
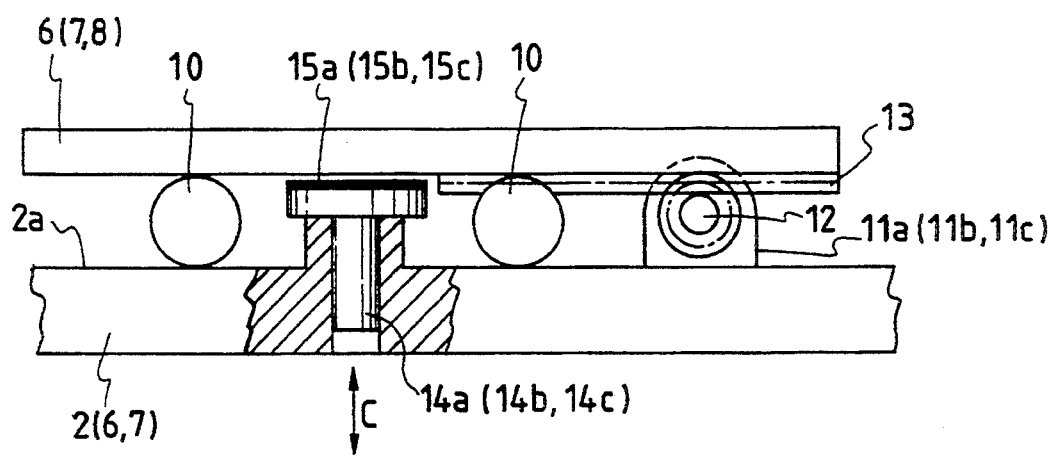
FIG. 3 is a sectional view illustrating, on an enlarged scale, main members of the microscope shifting device shown in FIG. 2.

FIG. 3 is a sectional view illustrating, on an enlarged scale, a structure for sustaining the first shifting member 6 relative to the surface 2a of the attaching member 2. In this drawing, the reference numeral 10 represents a roller guide, the reference numeral 11a designates an encoder which is fixed to the attaching member 2 and outputs a signal representing an angle of rotation caused by a shift of the first shifting member 6, the reference numeral 12 designates a pinion which is fixed to a rotating shaft of the encoder 11a and engaged with a rack 13 formed on the first shifting member 6, and the reference numeral 14a denotes a piston shaft which has an electromagnet 15a fixed to one end thereof and is disposed freely movable relative to the attaching member 2 in a direction indicated by an arrow C. The electromagnet 15a is excited by driving signals provided from a driving circuit 27 to be described later for producing a magnetic attracting force between the electromagnet 15a and the first shifting member 6, thereby sustaining the location of the first shifting member 6 relative to the surface 2a. The first shifting member 6 and the electromagnet 15a have contacting portions which are made of a magnetic material. Furthermore, structures for sustaining the second shifting member 7 and the third shifting member 8 relative to the surface 6a of the first shifting member 6 and the surface 7a of the second shifting member 7 respectively are similar to that shown in FIG. 3, signals representing angles of rotations caused by shifts of the shifting members are output from encoders 11b and 11c (FIG. 5) which are fixed to the surfaces mentioned above, and locations of the second and third shifting members are sustained by piston shafts having electromagnets 15b and 15c respectively fixed thereto.

Figure 4:
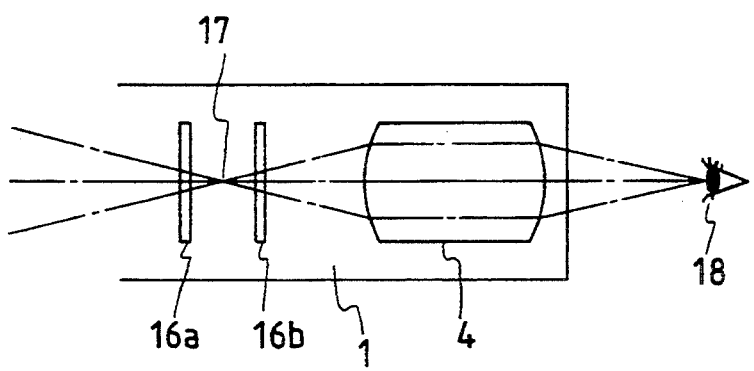
FIG. 4 is a sectional view illustrating an optical system disposed in the microscope shown in FIG. 2.

FIG. 4 is a sectional view illustrating the internal structure of the microscope 1 comprising the eyepiece lens 4. In this drawing, the reference numerals 16a and 16b represent focusing plates having marks such as cross hairs engraved thereon and disposed with a definite spacing reserved therebetween in the vicinity of an imaging point 17. The focusing plates 16a and 16b are to be observed by an eye of an operator through the eyepiece lens 4.

Figure 5:
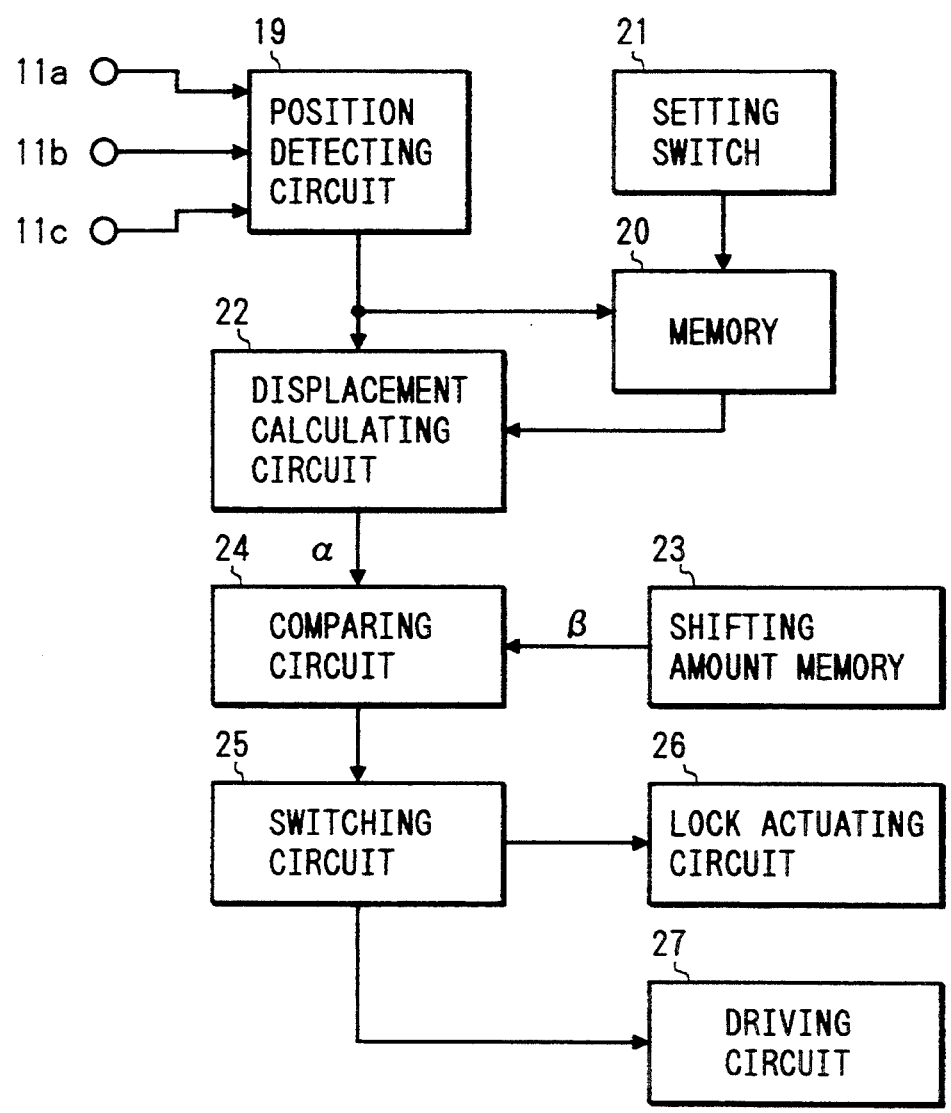
FIG. 5 is a block diagram of a drive control circuit to be used in the first embodiment of the present invention.

FIG. 5 is a block diagram of a circuit for driving and controlling the pupil location detecting device 5 and supporting device. In FIG. 5, the reference numeral 19 represents a position detecting circuit which detects values (x, y and z) on a three-dimensional coordinates system representing a location of the head rest 9 from signals of angles of rotations caused by shifts of the shifting members 6, 7 and 8 detected by the encoders 11a, 11b and 11c, and outputs signals corresponding to the values on the coordinates system. The reference numeral 20 designates a memory for temporarily storing, according to a signal provided from a setting switch 21, the signals expressing the location of the head rest 9 which have been detected by the position detecting circuit 19, and the reference numeral 22 denotes a displacement calculating circuit for calculating a displacement between the signals expressing the location of the head rest 9 temporarily stored by the memory 20 and signals expressing the location of the head rest 9 detected by the position detecting circuit 19 after the head rest 9 is shifted. When the signals expressing the location of the head rest 9 stored in the memory 20 are represented by ($x_s$, $y_s$ and $z_s$) and the signals expressing the location of the head rest 9 obtained after the head rest 9 is shifted are designated by (x, y and z), the displacement calculating circuit 22 calculates a displacement $\alpha$ by performing an operation expressed by the following formula (1):

$$\alpha = \sqrt{(x_s - x)^2 + (y_s - y)^2 + (z_s - z)^2} \quad (1)$$

The reference numeral 23 represents a memory for storing an allowable displacement $\beta$ which is to be used for shifting the head rest 9 in three dimensions within a range wherein the pupil of the operator does not deviate from the observing pupil of the microscope 1, and the reference numeral 24 designates a comparing circuit which compares the displacement $\alpha$ with the allowable displacement $\beta$ and outputs an operating signal to a switching circuit 25 immediately before the displacement $\alpha$ exceeds the allowable displacement $\beta$. Upon receiving the operating signal, the switching circuit 25 outputs driving signals to a lock actuating circuit 26 and a driving circuit 27, thereby driving and controlling the electromagnetic locks for the bearings BL1 through BL6 as well as the electromagnets 15a, 15b and 15c mounted on the supporting device.

Now, functions of the first embodiment of the present invention will be described. In an initial state, the electromagnetic locks on the supporting device are in an operating condition and the microscope 1 is held at a certain position. Furthermore, the electromagnets 15a, 15b and 15c are not excited, and the head rest 9 can be shifted freely relative to the microscope 1 by way of the attaching member 2, the first shifting member 6, the second shifting member 7 and the third shifting member 8.

An observer observes a magnified image of a part to be operated P through the eyepiece lens 4 in a condition where the head rest 9 is mounted and fixed on and to a head of the operator himself so that his pupil does not deviate from the head rest 9. Since rays emitted from the part to be operated on P are imaged at the imaging point 17 in the microscope 1, the operator can observe the cross hairs engraved as indices on the focusing plates 16a and 16b simultaneously with the magnified image of the part to be operated on P, whereby the operator can coincide a center of his pupil with the observing pupil of the microscope 1 simply by overlapping the center of his pupil with the cross hairs.

As for position information of the head rest 9 in the condition where the pupil of the observer is coincident with the observing pupil of the microscope 1, a position of the first shifting member 6 relative to the attaching member 2, a position of the second shifting member 7 relative to the first shifting member 6 and a position of the third shifting member 8 relative to the second shifting member 7 are sent from the encoders 11a, 11b and 11c respectively as rotating angle signals to the position detecting circuit 19, and converted into coordinates signals. By operating the setting switch 21, these signals are temporarily stored into the memory 20 as origin signals ($x_s$, $y_s$ and $z_s$) for the three-dimensional coordinates system at the location where the pupils are coincident with each other.

When the operator moves his head in an optional direction for shifting the microscope 1, position data representing a position of the first shifting member 6 relative to the attaching member 2, a position of the second shifting member 7 relative to the first shifting member 6 and a position of the third shifting member 8 relative to the second shifting member 7 are sent from the encoders 11a, 11b and 11c to the position detecting circuit 19, and converted into coordinates signals (x, y and z). Furthermore, the displacement calculating circuit 22 calculates a displacement $\alpha$ by performing the calculation expressed by the above-mentioned formula (1) by using the coordinates signals (x, y and z) and the origin signals ($x_s$, $y_s$ and $z_s$) stored in the memory 20, and outputs signals corresponding to the displacement to the comparing circuit 24.

The comparing circuit 24 reads out the allowable displacement $\beta$ from the memory 23, compares it with the displacement $\alpha$, and outputs an operating signal to the switching circuit 25 immediately before the displacement $\alpha$ exceeds the allowable displacement $\beta$. The switching circuit 25 releases all the electromagnetic locks on the supporting device by controlling the lock actuating circuit 26, and simultaneously feeds exciting currents to the electromagnets 15a, 15b and 15c by controlling the driving circuit 27. Three-dimensional shifting of the microscope 1 becomes possible upon releasing of the electromagnetic locks, whereas shifts of the first shifting member 6 relative to the attaching member 2, the second shifting member 7 relative to the first shifting member 6 and the third shifting member 8 relative to the second shifting member 7 are restricted since surfaces of the shifting members are attracted to the electromagnets by way of the piston shafts owing to the function of the electromagnets. Thereby, the head of the operator and the microscope 1 are fixed integrally at locations where the pupil of the operator is not deviated from the observing pupil of the microscope 1. Release of the head of the operator and the microscope 1 from the fixed condition, i.e., release of the driving circuit 27 by the switching circuit 25 can be performed, for example, by operating a well-known foot switch or similar means with a foot.

In a particular case where the first embodiment described above is mounted on a supporting device having such a structure as that shown in FIG. 1, the first embodiment is capable of detecting locations of the pupil of the operator relative to the microscope with the pupil location detecting device, freely shifting the microscope freely in three dimensions by way of the supporting device, and sustaining the head of the operator and the microscope integrally. Accordingly, the first embodiment makes it possible to move the microscope to follow shifts of the head or pupil of the observer without fail and is suited for use for surgical operations which require large and quick motions of operators. Furthermore, the first embodiment can be provided as an independent surgical microscope system since it can be composed by improving an eyepiece lens of the conventional surgical microscope apparatus such as that disclosed by Japanese Patent Preliminary Publication No. Sho 53-23168 and attaching the pupil detecting device to the improved eyepiece lens. Though the first embodiment is configured to detect a deviation of a pupil location as a variation of linear displacement in three dimensions from a position of an origin, it is needless to say that a deviation of a pupil location can also be detected by detecting a shift in only two directions of, for example, x and y, i.e., on a plane.

Figure 7:
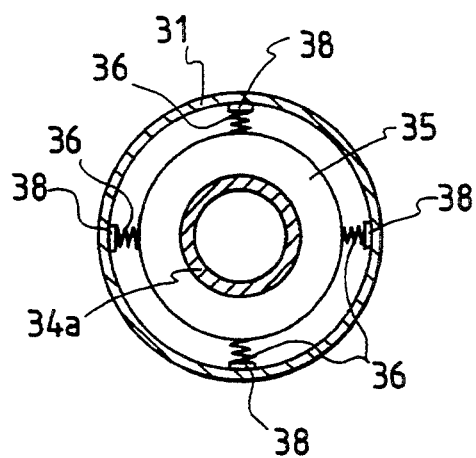
FIG. 7 is a sectional view taken along a line VII—VII in FIG. 6.
Figure 8:
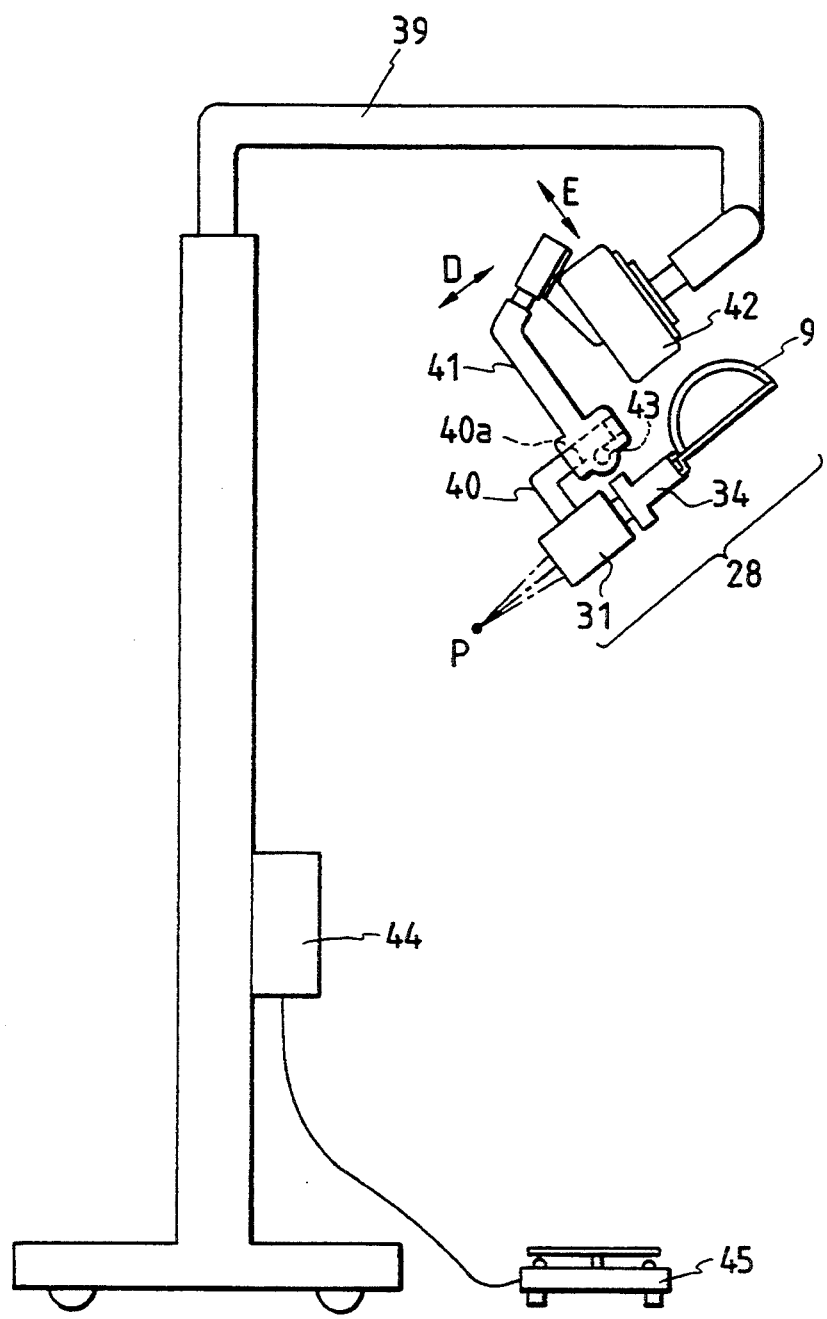
FIG. 8 is an external view illustrating the second embodiment of the surgical microscope apparatus according to the present invention.

Now, description will be made of the second embodiment of the present invention with reference to FIG. 6 through FIG. 8. In this embodiment, a microscope 28 consists of a first housing which comprises an objective lens 29 and an afocal vari-focal lens 30; and a second housing 34 which is coupled with the first housing 31 in a manner to be described later, comprises an imaging lens 32 and an eyepiece lens 33, and has a head rest 9.

For coupling the first housing 31 with the second housing 34, accommodated in a rear cavity of the first housing 31 is a collared cylinder 35 which is slidable in a direction perpendicular to the optical axis and engaged with a tip cylinder 34a formed at a tip of the second housing 34. A plurality of compression springs 36 are interposed between the tip cylinder 34a and the collared cylinder 35, and between the first housing 31 and the collared cylinder 35 respectively as shown in FIG. 6 and FIG. 7 so that the second housing 34 is sustained at a definite position (a position wherein the observing pupil of the microscope is coincident with the pupil of the operator) relative to the first housing 31. The reference numeral 37 represents a pushbutton switch which is disposed in opposition to the collared cylinder 35 and can be operated by a collar formed on a tip of the tip cylinder 34a and the reference numeral 38 designates another pushbutton which is disposed inside the first housing 31 and can be operated by an outer circumferential surface of the collared cylinder 35; these switches being connected to the drive controller attached to the supporting device. A mechanism for suspending the microscope 28 to an arm 39 of the supporting device is illustrated in FIG. 8, wherein the reference numeral 40 represents a supporting arm which is attached to the first housing 31 and has a rack 40a formed at a tip thereof, and the reference numeral 41 designates a supporting member which has an end attached to the arm 39 of the supporting device by way of a microscope shifting device 42 and the other end connected to the supporting arm 40 by way of a rack-pinion mechanism. Used as the microscope shifting device 42 is a mechanism which is like that disclosed by U.S. Pat. No. 4,714,328 (German Patent No. 31 47 836) and capable of moving the supporting member 41 in a direction indicated by an arrow E and another direction perpendicular to the surface of the drawing by a motor built in the microscope shifting device 42. Furthermore, the above-mentioned rack-pinion mechanism is structured by engaging a motor-driven pinion 43 attached to the end of the supporting member 41 by using bearings with the rack 40a of the supporting arm 40 slidably fitted over the end so that the microscope 28 is shifted in a direction indicated by arrow D when the pinion 43 is turned.

In addition, a rotating direction of a motor built in the microscope shifting device 42 and that of a motor for rotating the pinion 43 are determined dependently on a depressed position of a foot switch 45 when it is depressed by way of the drive controller 44.

Now, functions of the second embodiment of the present invention will be described. In case of the second embodiment also, an initial state of the microscope 28 is determined by adequately operating the foot switch 45 and the operator can observe a magnified image of the part to be operated on P in a condition where a head belt 9 is fixed to the head of the operator and his pupil is coincident with a pupil of emergence of the eyepiece lens 33. In the second embodiment, a light bundle is afocal in a section between the afocal vari-focal lens 30 and the imaging lens 32.

When the operator shifts the second housing 34 obliquely upward along the direction indicated by the arrow D for shifting the microscope 28 in the initial state, the switch 37 which is disposed in the rear cavity of the first housing 31 on a side near the second housing 34 is closed since it is depressed by the collar of the tip cylinder 34a of the second housing 34. Upon closing of the pushbutton switch 37, the drive controller 44 transmits a driving signal to the motor for rotating the pinion 43, thereby rotating the pinion 43 clockwise. Accordingly, the supporting arm 40 shifts the first housing 31 obliquely upward along the arrow D by way of the rack 40a. The first housing 31 thus shifts to follow the second housing 34. Upon releasing the pushbutton switch 37 from the depressed condition thereof, the pushbutton switch 37 is turned off and the pinion 43 stops rotating, thereby terminating the shift of the first housing 31. Furthermore, when the second housing 34 is shifted obliquely downward along the arrow D, the pushbutton switch 37 which is disposed on the side far from the second housing 34 is closed, and the pinion 43 is rotated counterclockwise by way of the drive controller 44 and the pinion driving motor. Accordingly, the first housing 31 is shifted obliquely downward along the arrow D and then stops shifting when the pushbutton switch 37 is released from the depressed condition thereof.

Figure 6:
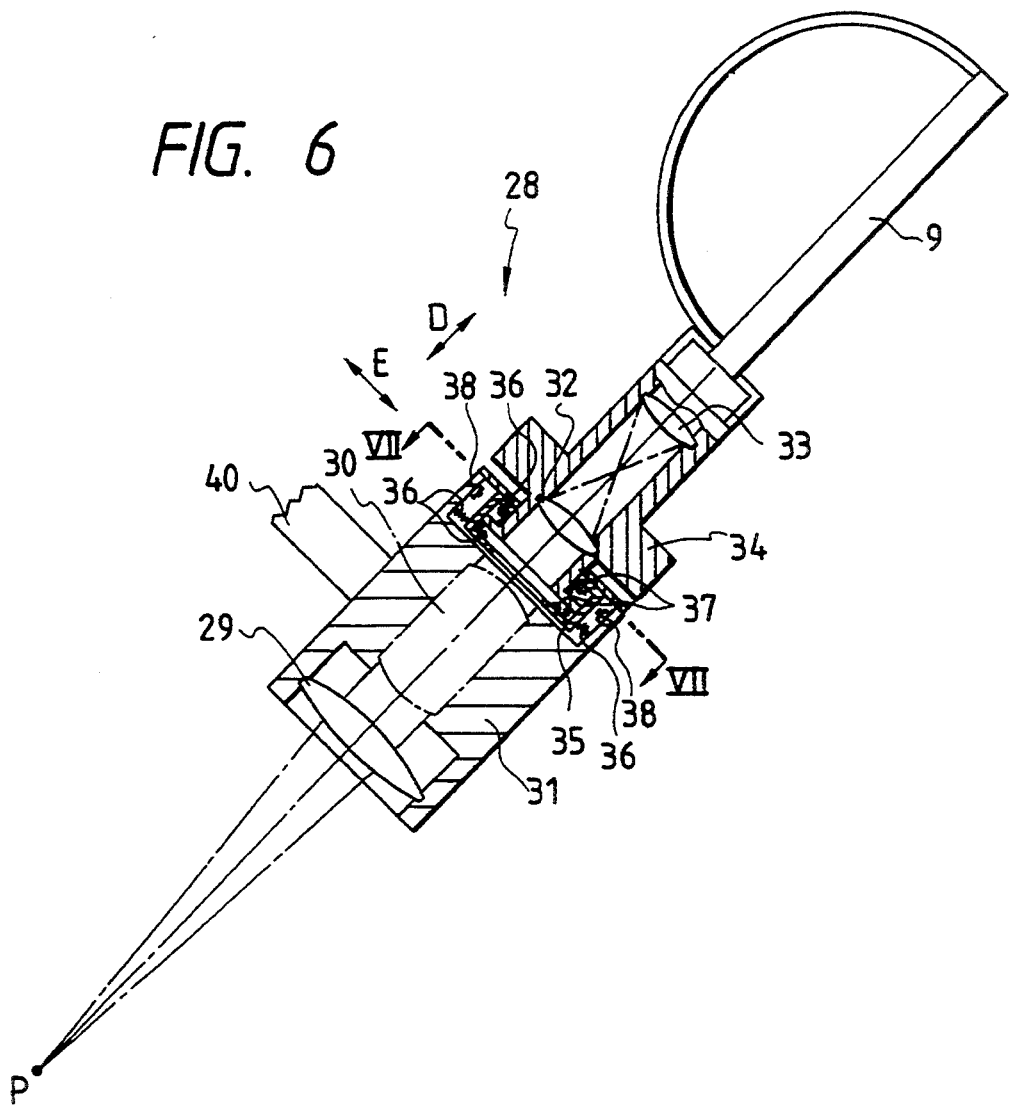
FIG. 6 is a longitudinal sectional view illustrating main members of a microscope to be used in a second embodiment of the surgical microscope apparatus according to the present invention.

Furthermore, when the operator shifts the second housing 34 along an arrow E by way of the head belt 9, the pushbutton 38 which is disposed on an upper side in FIG. 6 is closed since it is depressed by the collared cylinder 35. Upon closing of the pushbutton 38, the drive controller 44 transmits a driving signal to the motor built in the microscope shifting device 42 and the supporting member 41 is shifted obliquely upward along the arrow E due to rotation of the motor. The first housing 31 is thus shifted so as to follow the second housing 34 by way of the supporting arm 40. When the pushbutton switch 38 is released from the depressed condition thereof, the pushbutton switch 38 is turned off and the first housing 31 stops shifting. Functions of the microscope shifting device 42 will not be described here in detail since the functions are disclosed by the above-mentioned U.S. Pat. No. 4,714,328 (German Patent No. 31 47 836). When the second housing 34 is shifted obliquely downward along the arrow E, the pushbutton switch 38 which is disposed on a lower side in FIG. 6 is closed and the supporting member 41 is shifted obliquely downward along the arrow E by way of the drive controller 44 and the microscope shifting device 42. The supporting member 41 stops shifting when the pushbutton 38 is released from the depressed condition thereof. Since the pushbutton switches 38 are disposed at equal intervals as seen from FIG. 7, the first housing 31 can be shifted so as to follow the second housing 34 in a manner similar to that described above even when it is shifted in the direction perpendicular to the surface of the drawings.

Since the second embodiment is configured to project the pupil of the operator to an entrance pupil of the imaging lens 32 and detect a location thereof relative to an exit pupil of the afocal vari-focal lens 30 with the switches 37 and 38, the second embodiment has a simple configuration and is capable of shifting the microscope to follow a shift of the operator's head or pupil without fail. Though description of the second embodiment has been made about two cases where the microscope is shifted linearly in the directions along the arrow D and the arrow E, it is needless to say that the first housing 31 can follow the second housing 34 even when the latter housing is shifted in two or three dimensions.

Figure 9:
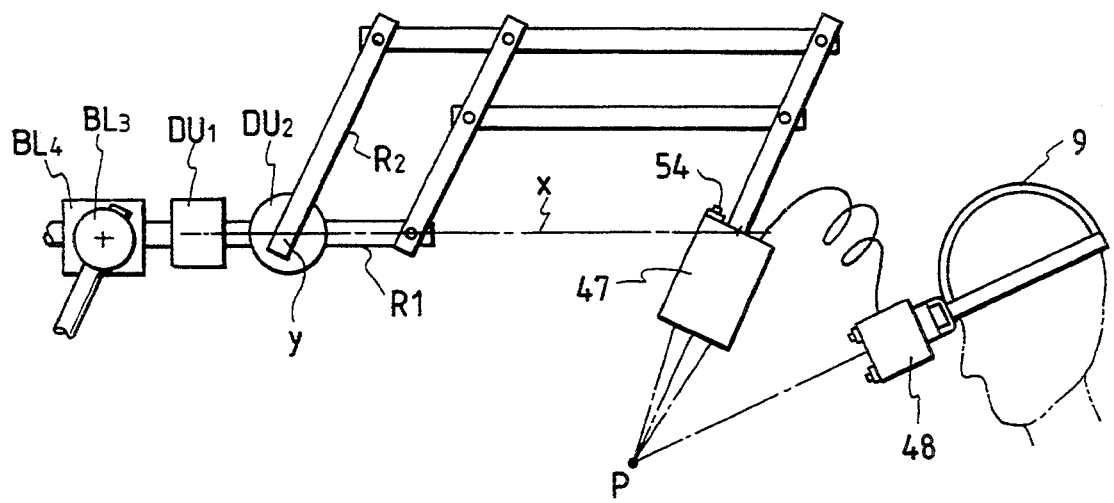
FIG. 9 is an external view illustrating a portion of a supporting device, a microscope shifting device and a microscope to be used in a third embodiment of the surgical microscope apparatus according to the present invention.
Figure 10:
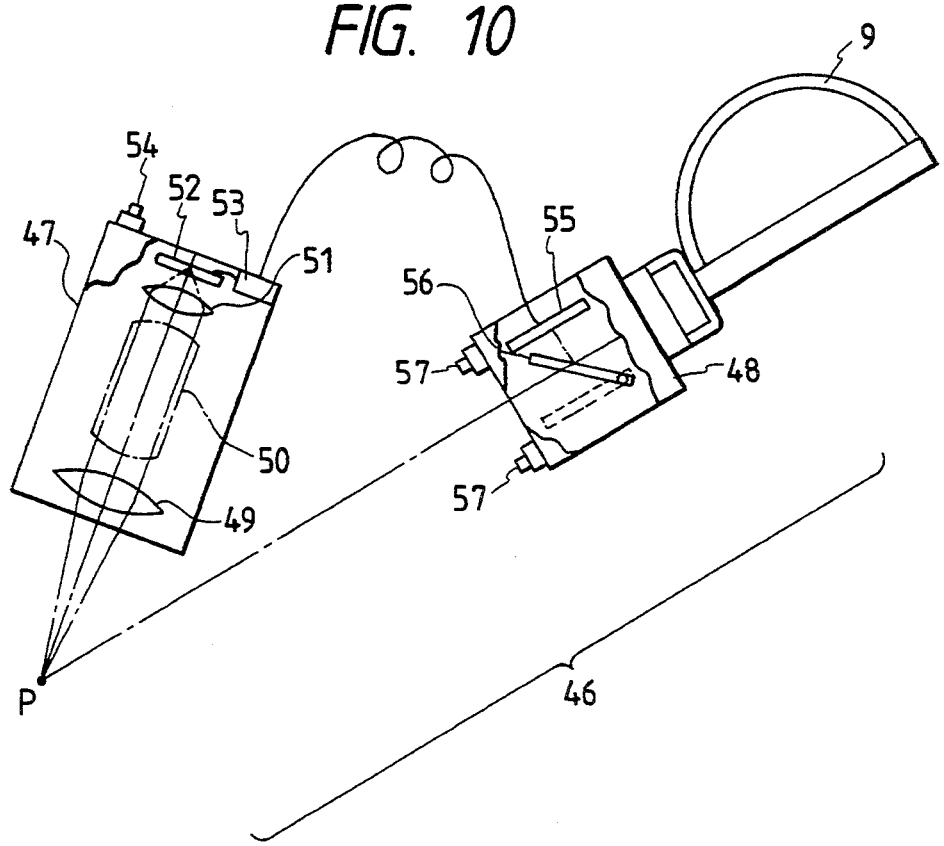
FIG. 10 is a partial sectional view illustrating an internal structure of the microscope used in the third embodiment on an enlarged scale.

Now, description will be made of the third embodiment of the present invention with reference to FIG. 9 through FIG. 11. In this embodiment, a microscope 46 consists of a first housing 47 which is attached to a supporting device and a second housing 48 which is to be fixed to a head of an operator by using a head belt 9 as illustrated in FIG. 9. Built in the first housing 47 are an objective lens 49, an afocal vari-focal lens 50, an imaging lens 51 and a video signal generating means 53 which functions to convert an image picked up by an image pickup element 52 into video signals. A supersonic oscillator 54 is attached to a rear end surface of the first housing 47. Built in the second housing 48 are a monitor 55 for displaying an image picked up by the image pickup element 52 by way of the video signal generating means 53 and a movable mirror 56 for leading, to an eye of an operator, an image displayed on the monitor 55 which is moved by solenoid etc. (not shown) to a position indicated by solid lines or another position indicated by dashed lines. Attached to a rear end surface of the second housing 48 are a pair of supersonic receivers 57. In addition, the supporting device shown in FIG. 9 is a little different in a structure of tip thereof from that illustrated in FIG. 1. The reference symbol $DU_1$ used in FIG. 9 represents a driving unit which has a built-in motor for revolving an arm $R_1$ around an x axis with a driving signal provided from a supporting arm control circuit to be described later and the reference symbol $DU_2$ designates another driving unit having a built-in motor for revolving an arm $R_2$ around a y axis perpendicular to the surface of the drawings with a driving signal provided from an arm control circuit to be described later. Furthermore, the supersonic oscillator 54 and the supersonic receiver 57 compose a position detecting device for detecting a position and an angle of the second housing 48 relative to the first housing 47.

Figure 11:
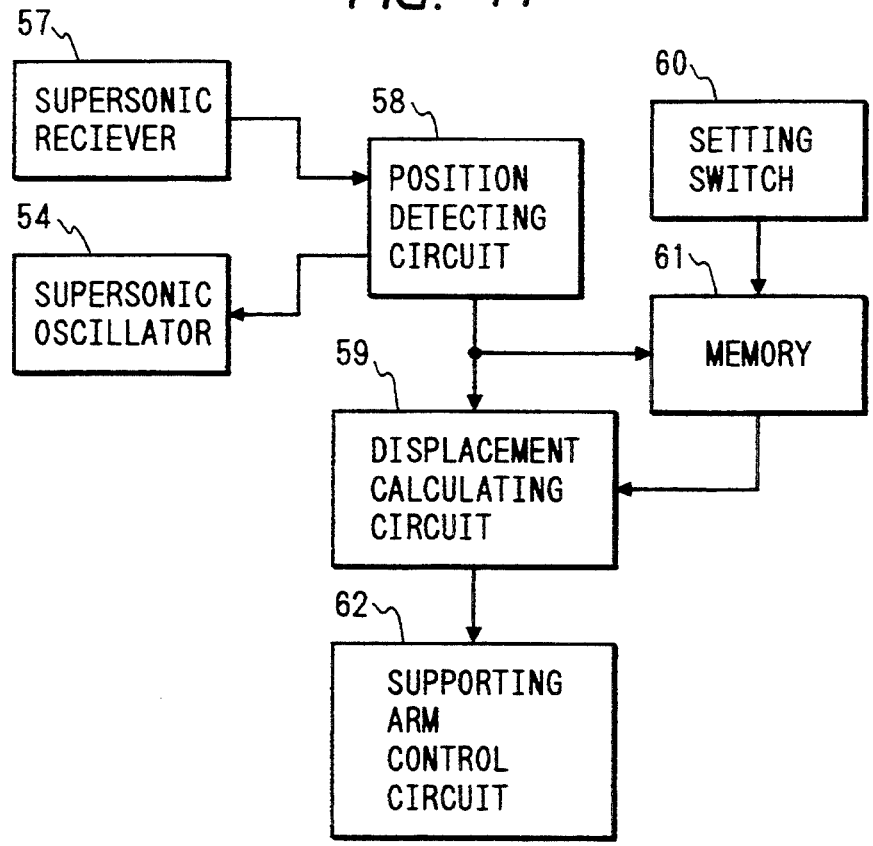
FIG. 11 is a block diagram illustrating a drive control circuit to be used in the third embodiment of the present invention.

FIG. 11 illustrates circuitry in a drive controller for the microscope 46 and the supporting device. In FIG. 11, the reference numeral 58 represents a position detecting circuit for detecting a spatial position of the second housing 48 relative to the first housing 47 by using the supersonic oscillator 54 and the supersonic receivers 57, the reference numeral 59 designates a displacement calculating circuit which calculates deviations of the microscope 46 from a location of an origin (an initial location) in x, y and z directions on the basis of three-dimensional coordinate signals provided from the position detecting circuit 58 and origin coordinates signals stored in a memory 61 by operating a setting switch 60, and the reference numeral 62 denotes a supporting arm control circuit which outputs driving signals to the driving units $DU_1$ and $DU_2$ for moving the supporting device in a direction corresponding to an output from the displacement calculating circuit 59.

Now, functions of the third embodiment of the present invention will be described. In a condition where the operator fixes his head to the head belt 9, he observes, while adequately moving the first housing 47, the magnified image of the part to be operated on P by way of the objective lens 49, the afocal vari-focal lens 50, the imaging lens 51, the image pickup element 52, the video signal generating means 53, the monitor 55 and the movable mirror 56. Upon operating the setting switch 60 after the operator shifts his head to a location which facilitates his work on the part to be operated on P, supersonic signals emitted from the supersonic oscillator 54 are received by the supersonic receivers 57, and information on a position and angle of the second housing 48 relative to the first housing 47 is supplied to the position detecting circuit 58. The information on the position and the angle which is supplied to the position detecting circuit 58 is converted into coordinates signals therein and temporarily stored in the memory 61 as an origin on a three-dimensional coordinates system.

When the operator shifts his head, i.e. the second housing 48 in an optional direction for shifting the microscope 46, information on a new position and angle of the second housing 48 is transmitted to the position detecting circuit 58, wherein the information is converted into three-dimensional coordinates signals as described above. A displacement on the coordinate system is calculated by the displacement detecting circuit 59 from the converted coordinates signals and the above-mentioned origin signals stored in the memory 61, driving signals corresponding to this displacement are output from the supporting arm control circuit 62 to the driving unit $DU_1$ and/or $DU_2$, etc. for shifting the first housing 47, and the shift of the first housing 47 is stopped when the displacement calculating circuit calculates a displacement of 0. The microscope 46 is shifted by the functions described above. Since the third embodiment is configured to shift the first housing 47 immediately before a calculated displacement exceeds the allowable displacement, the third embodiment may adopt a comparing circuit 24 like that of the first embodiment. Furthermore, when the movable mirror 56 is shifted to the position indicated by the dashed lines as occasion demands, the operator can directly observe the part to be operated on P as well as the operating tools.

Since the third embodiment is configured so as to allow the operator to observe the part to be operated on P by way of the monitor 55 as described above, the third embodiment allows a surgical operator to perform surgical operations at easy postures while selecting free positions of his head and set adequate values of the allowable displacement regardless of the observing pupil of the microscope 46, thereby assuring very simple use. Furthermore, the third embodiment is very practical since it permits directly observing the part to be operated on P as well as the operating tools.

Figure 12:
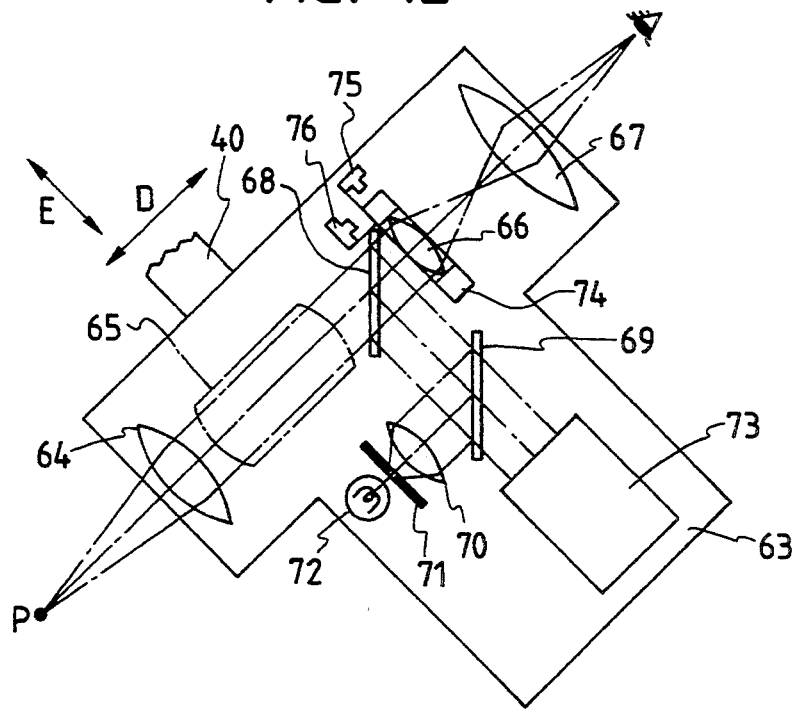
FIG. 12 is a sectional view illustrating an internal structure of a microscope to be used in a fourth embodiment of the surgical microscope apparatus according to the present invention.

Now, the fourth embodiment of the present invention will be described below with reference to FIG. 12 through FIG. 14. In FIG. 12, the reference numeral 63 represents a microscope of a surgical microscope apparatus which is supported by a supporting device similar to that shown in FIG. 8 by way of a supporting arm 40 and can be shifted by a motor driving device in directions indicated by arrows E and/or D. The reference numeral 64 designates an objective lens, the reference numeral 65 denotes an afocal vari-focal lens, the reference numeral 66 represents an imaging lens and the reference numeral 67 designates an eyepiece lens; these lenses compose an observing optical system of the microscope 63. The reference numeral 68 designates a first half mirror disposed in the observing optical system, the reference numeral 69 denotes a second half mirror, the reference numeral 70 represents a relay lens, the reference numeral 71 designates a light-transmitting index, the reference numeral 72 denotes a light source, the reference numeral 73 represents a device for detecting a location of an eye of an operator which has a composition such as that disclosed by Japanese Patent Preliminary Publication No. Hei 3-5810, the reference numeral 74 designates a lens frame which can be shifted by such a mechanism as that shown in FIG. 13 in a direction along an optical axis and/or a direction perpendicular to the optical axis, the reference numeral 75 represents second switches for detecting a shift in a direction perpendicular to the optical axis of the lens frame 74, i.e., in a direction indicated by an arrow E and the reference numeral 76 denotes first switches for detecting a shift in a direction along an optical axis of the lens frame 74, i.e., in a direction indicated by an arrow D; these members composing an optical system for detecting a location of an eye of an operator.

Figure 13:
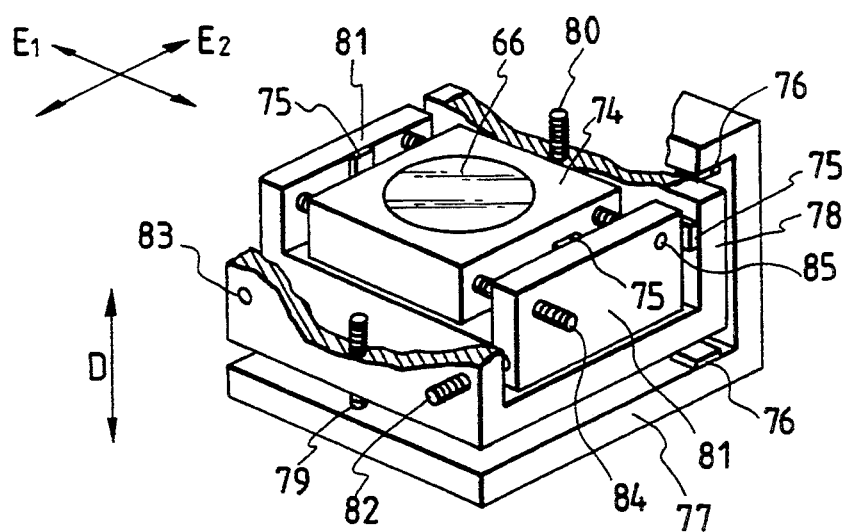
FIG. 13 is a partially broken perspective view illustrating a supporting device for an imaging lens to be used in the fourth embodiment of the present invention.

In FIG. 13, the reference numeral 77 represents a fixed frame to which the second switches 75 are attached, the reference numeral 78 designates a movable frame which is screwed over a guide screw 79 which is rotatably fitted into the fixed frame 77 and slidably guided by a guide rod 80 studded into the fixed frame 77, and the reference numeral 81 denotes a movable frame which is shiftably mounted on the movable frame 78 with a guide screw 82 and a guide rod 83 rotatably attached to the movable frame 78. The lens frame 74 is shiftably mounted on the movable frame 81 with a guide screw 84 and a guide rod 85 which are rotatably attached to the movable frame 81. The second switches 75 are attached to the movable frame 78 and the movable frame 81, and operated by the lens frame 74 and the movable frame 81 respectively. Furthermore, the first switches 76 are attached to the fixed frame 77 and operated by the movable frame 78. The guide screws 79, 82 and 84 are turned by motors (not shown) with outputs provided from the drive controller 44 shown in FIG. 8.

Figure 14A:
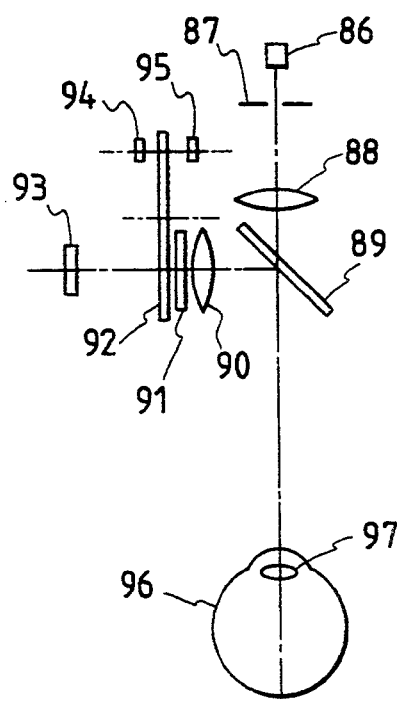
FIG. 14A is a sectional view illustrating an optical system for a device for detecting a location of a pupil of an observer which is to be used in the fourth embodiment of the present invention.
Figure 14B:
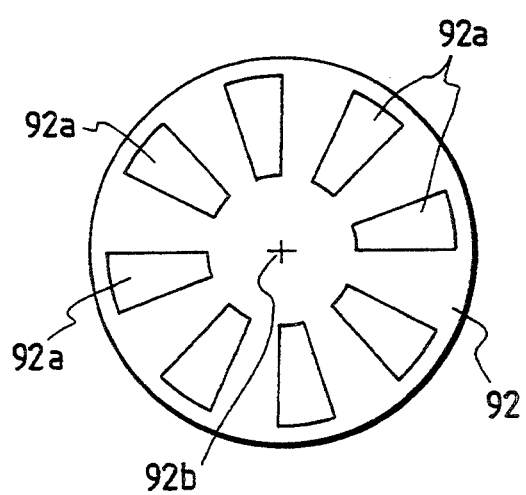
FIG. 14B is a front view of a chopper shown in FIG. 14A.

FIG. 14A illustrates a detecting optical system which is disposed in the device 73. In this drawing, the reference numerals 86, 87, 88 and 89 respectively, represent a light emitting element, a pinhole stop, a photographic lens and a half mirror which are disposed on a center axis line of an eye of the operator, and the reference numerals 90, 91, 92 and 93 respectively, designate an imaging lens, a stop, a chopper and two-dimensional light receiving element which are disposed on a reflecting optical axis from the half mirror 89, and the reference numerals 94 and 95 respectively, denote a light emitting element and a light receiving element respectively for standard signals which are disposed on both sides of the chopper 92. The chopper 92 is composed of a disk which has a plurality of sectorial slits 92a as shown in FIG. 14B and is disposed to be rotatable around a shaft 92b. An image of the pinhole stop 87 is imaged by the photographic lens 88 on a front portion 97 of the operator's eye 96 by way of the half mirror 89, reflected by a cornea of the eye 96, and imaged again on the two-dimensional light receiving element 93 by way of the half mirror 89, the imaging lens 90, the stop 91 and the slits 92a of the chopper 92. The fourth embodiment is capable of detecting a direction and a distance of a deviation of a vertex of the cornea of the eye 96 from a standard position on the basis of a variation of the imaging point on the light receiving element 93 which is caused by rotating the chopper 92.

Now, the function of the fourth embodiment will be explained below. The operator observes a magnified image of the part to be operated on P through the objective lens 64, the afocal vari-focal lens 65, the first half mirror 68, the imaging lens 66 and the eyepiece lens 67 while shifting the microscope 63 as a whole by using a foot switch 45 and a microscope shifting device 42 such as those shown in FIG. 8. On the other hand, an image of the front position of the operator's eye is transmitted into the device 73 by way of the eyepiece lens 67, the imaging lens 66, the first half mirror 68 and the second half mirror 69, whereby a location of the eye or the pupil of the operator relative to the microscope 63 is detected. When the location of the operator's pupil deviated from the observing pupil of the microscope 63, the drive controller 44 (FIG. 8) outputs motor driving signals on the basis of a deviation signal detected with the device 63, whereby the guide screws 79, 82 and 84 are adequately turned for shifting the lens frame 74 until the deviation becomes zero. The first switch 76 and the second switch 75 are disposed at such locations that they are operated for zeroing the deviation by shifting the lens frame 74 immediately before a correctable limit point is reached. When the first switch 76 or the second switch 75 is operated due to the shift of the lens frame 74, the microscope shifting device 42 and/or rack-pinion device 40a-43 (FIG. 8) are operated by the outputs from the drive controller 44 (FIG. 8), whereby the observing pupil of the microscope can be coincident with the location of the operator's pupil by shifting the microscope 63 as a whole. In the fourth embodiment, the light source 72 is lit or flickered upon a shifting of the microscope 63, and information on the index 71 (for example, "microscope being shifted") is transmitted to the operator's eye through the relay lens 70, the second half mirror 69, the first half mirror 68, the imaging lens 66 and the eyepiece lens 67 for informing the operator of a fact that the supporting device i.e. the microscope 63 is being shifted.

As is understood from the foregoing description, the fourth embodiment of the present invention allows the operator to freely shift his head and eliminate the tedious procedure of fastening a head belt around his head, thereby permitting a surgical operator to concentrate his attention on a surgical operation.

What is claimed is:

1. A surgical microscope apparatus comprising:
    a microscope;
    supporting means for supporting said microscope and permitting a movement of said microscope in three dimensions;
    detecting means for detecting a location of a pupil of an observer relative to an observing pupil of said microscope; and
    drive control means connected to said detecting means, for actuating said supporting means on a basis of a result produced by said detecting means to thereby move said microscope observing pupil relative to said location of said pupil of said observer.

2. A surgical microscope apparatus comprising:
    a microscope comprising;
        a first housing comprising an objective lens and an afocal vari-focal lens,
        a second housing shiftable relative to said first housing and comprising an imaging lens, and an eyepiece lens, and
        coupling means for resiliently urging said first housing and said second housing relative to each other with an optical axis of said first and second housing being coincident with each other,
    supporting means for supporting said microscope and permitting a movement of said microscope in three dimensions;
    a microscope movement device suspended from said supporting means and connected to said microscope first housing; and
    detecting means for detecting a location of a pupil of an observer relative to an observing pupil of said microscope, said detecting means being arranged in association with said coupling means and comprising switch means and a head rest connected to said second housing;

said drive control means being connected to said detecting means for actuating said supporting means on a basis of a result produced by said detecting means to thereby move said observing pupil of said microscope relative to said location of said pupil of said observer, said drive control means being operated by at least one of said switch means when said second housing is shifted; and said first housing being shifted by said microscope movement device by an output issued from said drive control means.

3. A surgical microscope apparatus according to claim 1, wherein said detecting means detects a relative movement amount between said observer and said microscope, and said microscope is relatively movably connected to said observer.

4. A surgical microscope apparatus according to claim 1, wherein said detecting means detects a relative movement amount between said observer and said microscope without connecting said microscope to said observer.

5. A surgical microscope apparatus comprising:
a microscope comprising:
   a first housing comprising an objective lens, an afocal vari-focal lens, an imaging lens, an image pickup element and a supersonic oscillator,
   a second housing comprising a monitor connected to said image pickup element to display a picked up image,
   a mirror for leading an image displayed on said monitor to an eye of said observer, and
   a supersonic receiver,
supporting means for supporting said microscope and permitting a movement of said microscope in three dimensions;
detecting means for detecting a location of a pupil of an observer relative to an observing pupil of said microscope comprising a head rest; and
drive control means connected to said detecting means, for actuating said supporting means on a basis of a result produced by said detecting means to thereby move said observing pupil of said microscope relative to said location of said pupil of said observer, said drive control means being operated on a basis of an output issued from said supersonic receiver when said second housing is shifted; and said first housing being shifted by an output provided from said drive control means.

6. A surgical microscope apparatus comprising:
a microscope comprising:
   an objective lens,
   an afocal vari-focal lens,
   a first half mirror,
   an imaging lens device mounted to be movable in directions along an optical axis and perpendicular to said optical axis,
   switch means disposed in association with said imaging lens device,
   an eyepiece lens, and
   eye detecting means for receiving rays reflected by said first half mirror and for detecting a position of an eye of an observer, and
supporting means for supporting said microscope to permit a movement of said microscope in three dimensions;
detecting means for detecting a location of a pupil of an observer relative to an observing pupil of said microscope; and
drive control means connected to said detecting means and said switch means, for actuating said supporting means on a basis of a result produced by said detecting means to thereby move said observing pupil of said microscope relative to said location of said pupil of said observer;
said imaging lens device being moved by said drive control means on a basis of an output issued from said eye detecting means when a deviation of said pupil of said observer from said observing pupil of said microscope is detected by said eye detecting means.

7. A surgical microscope apparatus according to claim 6, wherein said microscope further comprises:
   a second half mirror disposed adjacent to said first half mirror;
   a light source for leading rays to said second half mirror;
   an index; and
   a relay lens;
wherein said microscope is moved by driving said supporting means according to an output issued from said drive control means to coincide said observing pupil thereof with said pupil of said observer; and
wherein said light source is lit when said switch means is operated by said imaging lens device.

* * * * *